United States Patent
Dolgin (10) Patent No.: US 10,842,515 B2
(45) Date of Patent: Nov. 24, 2020

(54) ELECTRO-HYDRAULICALLY ACTUATED LITHOTRIPTERS AND RELATED METHODS

(71) Applicant: C.R. BARD, INC., Murray Hill, NJ (US)

(72) Inventor: Michael Dolgin, Cincinnati, OH (US)

(73) Assignee: C.R. BARD, INC., Murray Hill, NJ (US)

( * ) Notice: Subject to any disclaimer, the term of this patent is extended or adjusted under 35 U.S.C. 154(b) by 494 days.

(21) Appl. No.: 15/527,618

(22) PCT Filed: Nov. 24, 2015

(86) PCT No.: PCT/US2015/062476
§ 371 (c)(1),
(2) Date: May 17, 2017

(87) PCT Pub. No.: WO2016/089683
PCT Pub. Date: Jun. 9, 2016

(65) Prior Publication Data
US 2017/0360461 A1    Dec. 21, 2017

Related U.S. Application Data

(60) Provisional application No. 62/087,084, filed on Dec. 3, 2014.

(51) Int. Cl.
*A61B 17/22* (2006.01)
(52) U.S. Cl.
CPC .... *A61B 17/22012* (2013.01); *A61B 17/2202* (2013.01); *A61B 2017/22021* (2013.01); *A61B 2017/22025* (2013.01)

(58) Field of Classification Search
CPC . A61B 17/225; A61B 18/26; A61B 2018/263; A61B 2017/22011;
(Continued)

(56) References Cited

U.S. PATENT DOCUMENTS 4,191,189 A * 3/1980 Barkan ............ A61B 17/22022
606/128
5,224,942 A * 7/1993 Beuchat ................ A61B 18/26
606/128

(Continued)

OTHER PUBLICATIONS

International Search Report and Written Opinion from International Application No. PCT/US2015/062476 dated Feb. 9, 2016.

*Primary Examiner* — Gregory A Anderson
(74) *Attorney, Agent, or Firm* — Dorsey & Whitney LLP (57) ABSTRACT

Embodiments are directed to electro-hydraulically actuated lithotripters and methods for fragmenting stones using such lithotripters. In an embodiment, a lithotripter apparatus for fragmenting at least one stone in a body is disclosed. The lithotripter apparatus includes a chamber configured to contain an electro-conductive fluid, which includes a proximal end wall and a distal end wall spaced from the proximal end wall. A chisel is coupled to the chamber and located at least proximate to the distal end wall. A proximal electrode is located at least partially in the chamber. A distal electrode is located at least partially in the chamber and spaced from the proximal electrode. Responsive to an effective voltage applied between the proximal and distal electrodes, the proximal and distal electrodes are configured to electrically discharge into the electro-conductive fluid to generate shock waves in the chamber that accelerate the chisel toward the at least one stone.

24 Claims, 3 Drawing Sheets

(58) Field of Classification Search
CPC ........ A61B 17/22004; A61B 17/22012; A61B 17/2202; A61B 2017/22021; A61B 2017/22025
See application file for complete search history.

(56) References Cited

U.S. PATENT DOCUMENTS

| | | |
|---|---|---|
| 5,906,623 A | 5/1999 | Peterson et al. |
| 5,944,687 A * | 8/1999 | Benett .................... A61B 18/26 604/22 |
| 2004/0010267 A1 | 1/2004 | Nakamura et al. |
| 2008/0191596 A1 * | 8/2008 | King .................... A61B 17/225 313/165 |
| 2010/0036294 A1 | 2/2010 | Mantell et al. |
| 2014/0052146 A1 * | 2/2014 | Curtis ............. A61B 17/22022 606/128 |

* cited by examiner

ELECTRO-HYDRAULICALLY ACTUATED LITHOTRIPTERS AND RELATED METHODS

CROSS-REFERENCE TO RELATED APPLICATIONS

This application claims priority to U.S. Provisional Application No. 62/087,084 filed on 3 Dec. 2014, the disclosure of which is incorporated herein, in its entirety, by this reference.

BACKGROUND

The application of acoustic energy pulses ("acoustic pulses") or shock waves to living tissue, known as extracorporeal shockwave lithotripsy ("ESWL"), has become a common approach for performing non-invasive surgical procedures on living beings. For example, acoustic pulses can be applied externally to living tissue of a person to facilitate breakdown and removal of internal concretions, such as kidney stones. Another common application of acoustic pulses to living tissue is known as extracorporeal shockwave therapy ("ESWT"), which is typically used to perform non-invasive internal treatment of orthopedic conditions, such as plantar fasciitis which is a painful, chronic disorder of soft tissue near the heel of the foot.

Several techniques have been used to generate shock waves and fragment kidney stones including mechanical lithotripters, electro-hydraulic lithotripters, and laser lithotripters. Duration and safety of stone removal procedure may vary from one patient to the next and may depend, among other things, on the tools and methods used during the procedure.

Mechanical lithotripters are based on energy from a generator, usually from compressed gas or energy from a projectile accelerated by an electromagnetic field. For example, the ballistic energy from the projectile can be transferred to the object to be destroyed or fragmented, which may be brittle. For example, kidney stones can fragment upon impact by the mechanical lithotripter, which generally has a high success in delivering energy to the object and a low level of complications. However, the mechanical lithotripter is relatively rigid, which prevents from being used with flexible scopes.

Electro-hydraulic lithotripters use electrodes to electrically discharge in an electrically conductive liquid to create high-pressure waves or hydraulic shock waves, which cause cavitation bubbles in the liquid surrounding the stones. The cavitation bubbles in the living tissue may contribute to the fragmentation of the targeted stones, such as the kidney stones, by releasing energy in the vicinity of the stones and thus destroy the kidney stones. Cavitation is the formation of vapor cavities (e.g. bubbles or voids) in a liquid. When a liquid is subjected to rapid changes of pressure (e.g. a hydraulic shock wave), cavities may be formed near where the pressure is relatively low. When subjected to higher pressure, the voids can implode and generate an intense shock wave. The cavitation bubbles may occur in the living tissue or body part by the stone. Also, the size and/or amount of the cavitation bubbles may be selectively varied. For example, if the amount and/or voltage of electric pulses that are applied to living tissue are increased, the cavitation bubbles that are generated may increase in size and/or amount. Similarly, if the amount or voltage of electric pulses that are applied to living tissue are decreased, the cavitation bubbles that are generated may decrease in size and/or amount, or the bubble generation may fall below a productive threshold (e.g., the bubble generation may cease). However, the hydraulic shock waves may damage tissue through which the hydraulic shock waves pass and the cavitation bubbles may damage surrounding tissue when the cavitation bubbles implode. The electro-hydraulic lithotripters generally use inexpensive generators and disposables, but may be risky for causing tissue damage.

Accordingly, users and manufacturers of stone removal tools continue to seek tools and methods for fragmenting kidney stones with improved safety.

SUMMARY

Embodiments disclosed herein are directed to electro-hydraulically actuated lithotripters, lithotripter apparatuses using such electro-hydraulically actuated lithotripters, and methods for fragmenting stones using such electro-hydraulically actuated lithotripters. The electro-hydraulically actuated lithotripters disclosed herein are configured to electro-hydraulically drive a chisel into a stone to be at least partially destroyed, such as fragmented.

In an embodiment, a lithotripter apparatus for fragmenting at least one stone in a body during medical treatment is disclosed. The lithotripter apparatus includes a chamber configured to contain an electro-conductive fluid therein. The chamber includes a proximal end wall, a distal end wall spaced from the proximal end wall, and an intermediate portion therebetween. The lithotripter apparatus further includes a chisel coupled to the chamber and located at least proximate to the distal end wall. The lithotripter apparatus also includes a proximal electrode located at least partially in the chamber, and a distal electrode located at least partially in the chamber and spaced from the proximal electrode. Responsive to an effective voltage applied between the proximal and distal electrodes, the proximal and distal electrodes are configured to electrically discharge into the electro-conductive fluid to generate shock waves in the chamber that accelerate the chisel.

In an embodiment, a method of using a lithotripter apparatus for fragmenting at least one stone in a body during medical treatment is disclosed. The method includes positioning a chisel at or near the at least one stone in the body. The chisel is coupled to a chamber that contains an electro-conductive fluid therein. The method further includes applying a voltage to a proximal electrode located at least partially in the chamber and a distal electrode located at least partially in the chamber and spaced from the proximal electrode. Applying the voltage to the proximal electrode and the distal electrode causes electrical discharge into the electro-conductive fluid from the proximal electrode and the distal electrode and generation of shock waves in the chamber that accelerate the chisel toward the at least one stone.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

For better understanding, like elements have been designated by like reference numbers throughout the various accompanying figures. Understanding that these drawings depict only typical embodiments of the disclosure and are not therefore to be considered to be limiting of its scope, the embodiments of the disclosure will be described and explained with additional specificity and detail through the use of the accompanying drawings in which.

DETAILED DESCRIPTION

Embodiments disclosed herein are directed to electro-hydraulically actuated lithotripters, lithotripter apparatuses using such electro-hydraulically actuated lithotripters, and methods for fragmenting stones using such electro-hydraulically actuated lithotripters, such as kidney stones, gallstones, cystine stones, and other calculi. The electro-hydraulically actuated lithotripters disclosed herein are electro-hydraulically actuated such that shock waves are generated in a chamber that drives a chisel coupled thereto into a stone to be at least partially destroyed, such as fragmented. The shock waves are substantially contained in the chamber, thereby preventing or limiting damage to tissue surrounding the stone.

In one or more embodiments, a lithotripter apparatus including an electro-hydraulically actuated lithotripter for fragmenting a stone in a body during medical treatment is disclosed. The lithotripter apparatus includes a chamber configured to contain an electro-conductive fluid therein. The chamber includes a proximal end wall, a distal end wall spaced from the proximal end wall, and an intermediate portion therebetween. A chisel may be coupled to the chamber and located at least proximate to the distal end wall. A proximal electrode may be located at least partially in the chamber and may be located, for example, at or near the proximal end wall. A distal electrode may be located at least partially in the chamber, for example, at or near the distal end wall. The distal electrode may be spaced from the proximal electrode.

The chamber is configured to be expanded substantially in a longitudinal axial direction under internal pressure, with the distal end wall being substantially more expandable and/or longitudinally displaceable than the proximal end wall. For example, the proximal end wall of the chamber may be supported or may have a relatively high mass compared to the distal end wall. As such, the proximal end wall may not be substantially expanded and/or longitudinally displaced in response to electrical discharge from the proximal and distal electrodes. The shock waves may be directly formed by the electrical discharge and/or indirectly from cavitation generated by the electrical discharge However, it should also be understood that the chamber may also experience a certain amount of expansion and/or contraction in a radial direction under the internal pressure and/or the longitudinal displacement.

Responsive to an effective voltage applied between the proximal and distal electrodes, the proximal and distal electrodes electrically discharge into the electro-conductive fluid. The electrical discharge may generate an internal pressure due to shock waves formed by the electrical discharge. The shock waves may be directly formed by the electrical discharge and/or indirectly from cavitation generated by the electrical discharge. The internal pressure in the chamber may accelerate at least the distal end of the chamber and the chisel associated therewith in the longitudinal axial direction toward the stone to be fragmented. The accelerated chisel may impact at least one stone in the body and at least partially destroy the stone.

Figure 1:
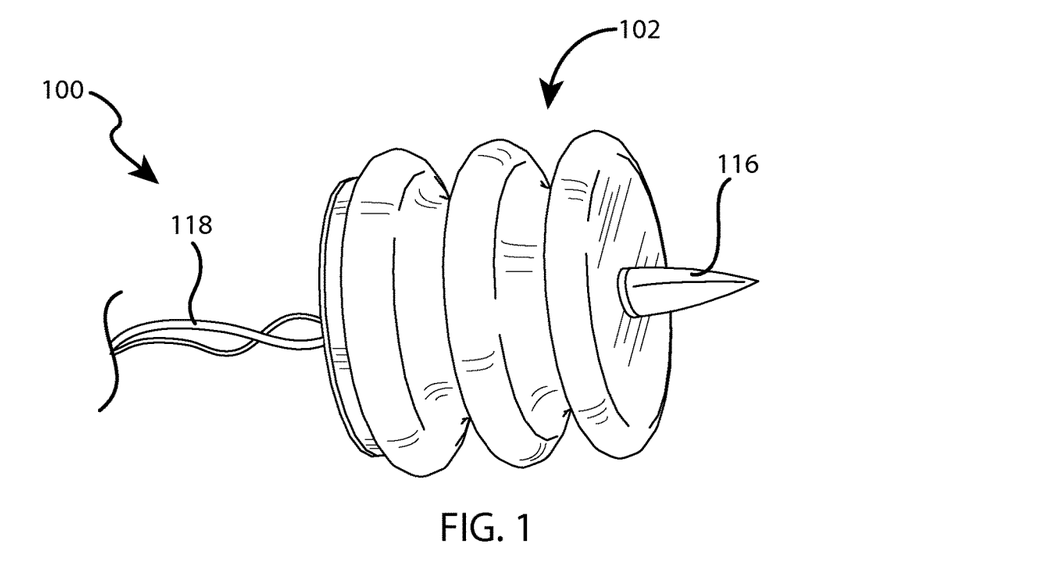
FIG. 1 is an isometric view of an electro-hydraulically actuated lithotripter according to an embodiment.
Figure 2:
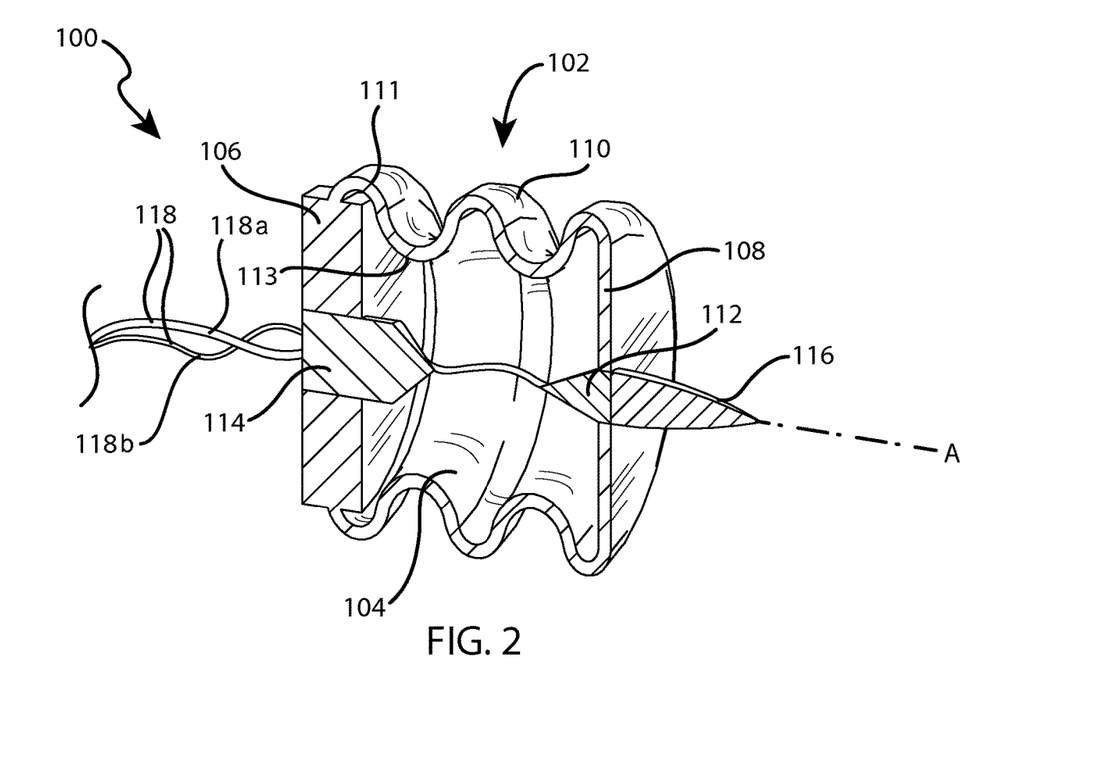
FIG. 2 is an isometric cutaway view of the electro-hydraulically actuated lithotripter of FIG. 1 according to an embodiment.

FIGS. 1 and 2 are isometric and isometric cutaway views, respectively, of an electro-hydraulically actuated lithotripter 100 according to an embodiment. The electro-hydraulically actuated lithotripter 100 includes a chamber 102 filled or configured to be filled with an electro-conductive fluid 104. For example, the electro-conductive fluid 104 may include a 0.5% solution of sodium chloride or another solution including water and one or more salts. The chamber 102 may be substantially sealed with the electro-conductive fluid 104 therein. As will be discussed in more detail below, the chamber 102 is configured to help substantially contain shock waves generated therein by electrical discharge into the electro-conductive fluid 104 in order to avoid or limit damage to tissue around the electro-hydraulically actuated lithotripter 100 and/or a stone that is to be destroyed by such shock waves.

The chamber 102 further includes a proximal end wall 106 (e.g., back wall), a distal end wall 108 (e.g., front wall) spaced from the proximal end wall 106, and an intermediate portion 110 located therebetween. In an embodiment, the distal end wall 108 of the chamber 102 may be configured to be displaced in a longitudinal axial direction A responsive to shock waves generated inside the chamber 102, while the proximal end wall 106 may be configured to not be substantially displaced responsive to shock waves generated inside the chamber 102. The distal end wall 108 may further be configured to substantially recover or relax to its original position when the shock waves dissipate. For example, the proximal end wall 106 may be supported and/or connected to a rigid or semi-rigid structure, such as an endoscope. In an embodiment, the distal end wall 108 of the chamber 102 may be relatively thinner than the proximal end wall 106 of the chamber 102. For example, the proximal end wall 106 may be at least five times thicker than the distal end wall 108. For example, the proximal end wall 106 may exhibit a thickness of about 0.20 mm to about 0.50 mm (e.g., about 0.25 mm to about 0.40 mm) and the distal end wall 108 may exhibit a thickness of about 0.015 mm to about 0.10 mm (e.g., 0.020 mm to about 0.040 mm, 0.025 mm to about 0.050 mm, or about 0.020 mm to about 0.35 mm). In an embodiment, the distal end wall 108 of the chamber 102 may be relatively lighter than the proximal end wall 106 of the chamber 102. For example, the proximal end wall 106 may be at least about five times heavier (e.g., at least about 10 time heavier, about 5 to about 30 times heavier) than the distal end wall 108. The chamber 102 including the proximal end wall 106, the distal end wall 108, and the intermediate portion 110 may be sufficiently thick enough in combination with the material from which it is made such that the chamber 102 is not substantially permeable to shock waves so that damage to tissue surrounding the at least one stone and/or the chamber 102 is limited or prevented during operation of the electro-hydraulically actuated lithotripter 100.

The intermediate portion 110 of the chamber 102 is further configured to be longitudinally flexible in the longitudinal axial direction A. For example, the chamber 102 may be substantially cylindrical and the intermediate portion 110 of the chamber 102 may exhibit an outer diameter of about 1 mm to about 3 mm (e.g., about 1.5 mm to about 2.5 mm, or about 2 mm) and a wall thickness of about 0.01 mm to about 0.05 mm (e.g., about 0.01 mm to about 0.02 mm).

In an embodiment, the intermediate portion 110 may be configured as a bellows so that the intermediate portion 110 is longitudinally expandable and compressible. For example, the intermediate portion 110 may include one or more protrusions 111 interleaved with one or more recesses 113, wherein the protrusions 111 protrude and the recesses 113 are recessed relative to a radial direction of the chamber 102. The protrusions 111 and recesses 113 provide longitudinal flexibility to the intermediate portion 110 of the chamber 102.

The chamber 102 may be formed of an electrical insulator or a metallic material. For example, the chamber 102 may be formed from a flexible, electrically insulating material, such as an elastomer, a thermoplastic, or other polymeric material. As another example, the chamber 102 may also be formed of a suitable stainless steel, a titanium alloy, or another suitable alloy or medical grade alloy.

In one specific embodiment, the intermediate portion 110 of the chamber 102 may exhibit an outer diameter of about 1 mm to about 4 mm (e.g., 2 mm) and a wall thickness of about 0.01 mm to about 0.002 mm (e.g., 0.01 mm), the proximal end wall 106 may exhibit a thickness of about 0.20 mm to about 0.50 mm, the distal end wall 108 may exhibit a thickness of about 0.015 mm to about 0.05 mm (e.g., 0.020 mm), and the entire chamber 102 may be formed from a stainless steel such as an austenitic 316 stainless steel, a martensitic 420 or 440 stainless steel, or Ti-6Al-4V.

The electro-hydraulically actuated lithotripter 100 further includes a distal electrode 112 coupled to the distal end wall 108 and a proximal electrode 114 coupled to the proximal end wall 106. The distal electrode 112 and proximal electrode 114 are located at least partially inside the chamber 102. However, in other embodiments, the distal electrode 112 and/or the proximal electrode 114 may not be coupled to the distal end wall 108 and/or proximal end wall 106, respectively. For example, at least one of the distal electrode 112 or the proximal electrode 114 may be coupled to a portion of the intermediate portion 110 near the distal end wall 106 and the proximal end wall 106, respectively. In the illustrated embodiment, the proximal electrode 114 extends from the proximal end wall 106 inwardly along the longitudinal axial direction A toward the distal end wall 108. For example, the proximal end wall 106 may include an opening therein and the proximal electrode 114 may extending inwardly through the opening. The proximal electrode 114 may include a sharpened tip portion effective for electrical discharging into the electro-conductive fluid 104. The distal electrode 112 may also extend inwardly along the longitudinal axial direction A toward the proximal end wall 106. For example, the distal end wall 108 may include an opening therein and the distal electrode 112 may extending inwardly through the opening. The distal electrode 112 may also include a sharpened tip portion also effective for electrical discharging into the electro-conductive fluid 104 that extends toward the tip portion of the proximal electrode 114.

The tip portion of the distal electrode 112 and the tip portion of the proximal electrode 114 define a gap therebetween. The gap and the electro-conductive fluid 104 may affect a minimum voltage at which electrical discharge occurs into the electro-conductive fluid 104. For example, the gap may be about 0.25 mm to about 0.75 mm, such as about 0.40 mm to about 0.6 mm, or about 0.5 mm. For example, when the electro-conductive fluid 104 is 0.5% solution of sodium chloride and the gap is about 0.5 mm, the minimum voltage at which electrical discharge occurs may be about 1 kV to about 6 kV. In an embodiment, electrically conductive additives (e.g., gold nanoparticles, silver nanoparticles, or other metallic nanoparticles) may be added to the electro-conductive fluid 104 to reduce the minimum voltage at which discharge occurs. The gap may increase during electrical discharging into the electro-conductive fluid 104 because, as previously discussed, the distal end wall 108 may be displaced along the longitudinal direction A in response to the electrical discharging.

The proximal electrode 114 and distal electrode 112 may be formed from a suitable electrically conductive material. For example, each of the proximal electrode 114 and distal electrode 112 may be formed of an electrically conductive material including, but not limited to, copper, aluminum, silver, gold, alloys thereof, combinations thereof, or other suitable material.

The electro-hydraulically actuated lithotripter 100 may also include a chisel 116 coupled to the chamber 102 and configured for direct contact (e.g., impact) with an object to be fragmented. For example, the chisel 116 may include a shaped cutting edge and/or tip configured to cut or fracture a hard material, such as stones or other calculi. The chisel 116 may be made from a relatively hard, wear resistant material. For example, the chisel 116 may be made from steel, stainless steel, titanium, tungsten carbide, or other biocompatible material.

The chisel 116 may be coupled to the chamber 102 and located proximate to the distal end wall 108. For example, the chisel 116 may be coupled to the distal end wall 108. In the illustrated embodiment, the chisel 116 may be coupled to an end of the distal electrode 112 opposite the tip portion thereof. For example, the chisel 116 may be separately formed and attached to the distal electrode 112, or the chisel 116 and the distal electrode 112 may be integrally formed with each other. In such an example, the distal electrode 112 and/or the chisel 116 may be coupled to the distal end wall 108. In another embodiment, the chisel 116 may be directly coupled to the distal end wall 108 instead of the distal electrode 112 or attached to the distal end wall 108 and the distal electrode 112.

The electro-hydraulically actuated lithotripter 100 further includes an electrical connection 118 electrically coupled to the proximal electrode 114 and the distal electrode 112. For example, the electrical connection 118 includes a first electrical connection 118a that is electrically coupled to the proximal electrode 114 and a second electrical connection 118b that is electrically coupled to the distal electrode 112. The second electrical connection 118b may be located inside the chamber 102 (e.g., submerged in the electro-conductive fluid 104), outside the chamber 102, at least partially embedded in the body that defines the chamber 102, or combinations of the foregoing. Both the first electrical connection 118a and the second electrical connection 118b may extend outside of the chamber 102.

As will be discussed in more detail below, the electrical connections 118a and 118b may be coupled to a voltage generator (not shown) configured to apply an effective voltage between the proximal electrode 114 and distal electrode 112 for generating the electrical discharge in the electro-conductive fluid 104. The electrical connections 118a and 118b may be electrical wires, electrically conductive traces, other suitable electrically conductive structure, or combinations thereof. The electrical connections 118a and 118b may include sleeves formed of highly insulating material to be capable of sustaining electrical discharging. The electric connections 118a and 118b may be as long or short as needed or desired for a particular design of the electro-hydraulically actuated lithotripter 100.

In operation, a voltage is applied by a voltage generator (not shown) between the proximal electrode 114 and the distal electrode 112, which is effective to cause electrical discharge in the electro-conductive fluid 104. For example, the voltage generator is coupled to the electrical connections 118a and 118b that are respectively coupled to the proximal electrode 114 and the distal electrode 112. The electrical discharge directly generates shock waves inside of the chamber 102 that create internal pressure in the chamber 102. The electrical discharge may also generate cavitation that also generates shock waves in the chamber 102 that also create internal pressure in the chamber 102. The distal electrode 112 and/or distal end wall 108 may transmit the shock waves to the chisel 116, which causes the chisel 116 to accelerate and directly contact and/or impact the at least one stone. In particular, the internal pressure generated by the shock waves cause the chamber 102 to at least longitudinally expand, thereby causing at least the distal end wall 108 and the chisel 116 to move and accelerate in the longitudinally axial direction A. The impact causes the at least one stone to be at least partially destroyed, such as being fragmented into multiple smaller pieces. For example, the chisel 116 may move outwardly a small distance in the longitudinal axial direction A responsive to the shock waves generated in the chamber 102 during the electrical discharging. The small distance that the chisel 116 longitudinally moves may be about 0.50 mm to about 1.5 mm, such as about 0.75 mm to about 1 mm. The chisel 116 returns to its original position shown in FIGS. 1 and 2 when the shock waves dissipate. The proximal electrode 114 and the proximal end wall 106 may accelerate much less than the distal electrode 112 and the distal end wall 108 because, for example, the proximal end wall 106 is substantially thicker and heavier than the distal end wall 108.

Figure 3:
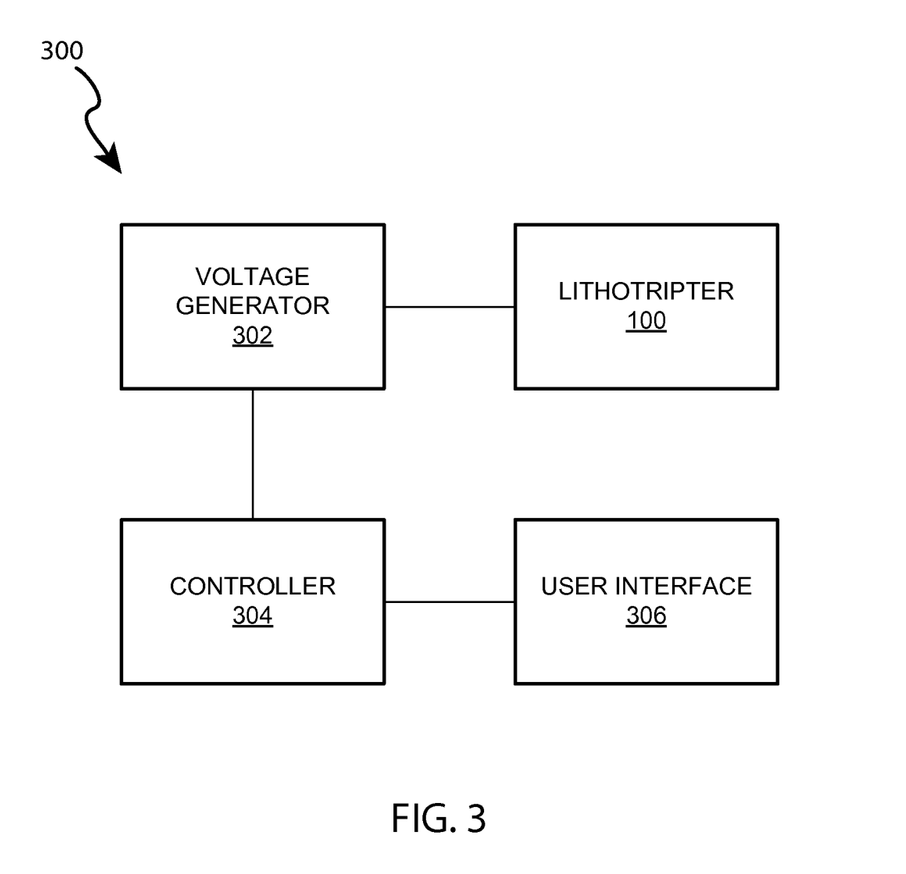
FIG. 3 is a simplified diagram for a lithotripter apparatus including the electro-hydraulically actuated lithotripter of FIGS. 1 and 2 according to an embodiment.

FIG. 3 is a simplified diagram for a lithotripter apparatus 300 including the electro-hydraulically actuated lithotripter of FIGS. 1 and 2 according to an embodiment. The lithotripter apparatus 300 includes a voltage generator 302 electrically coupled to the proximal and distal electrodes 114 and 112 of the electro-hydraulically actuated lithotripter 100 through the electrical connections 118a and 118b. The voltage generator 302 is configured to apply high electric voltages to the proximal and distal electrodes 114 and 112, which may generate electrical discharges in the electro-conductive fluid 104 inside the chamber 102. For example, the voltage generator 302 may be a battery, a variable voltage source, or other suitable power supply configured to apply a voltage. The electrical discharge may be in the form of hot plasma that is formed between the proximal electrode 114 and distal electrode 112 when high voltages are applied to the proximal and distal electrodes 114 and 112. The rapid expansion of the plasma leads to generation of shock waves in the chamber 102. The shock waves accelerate the distal end wall 108, the distal electrode 112, and the chisel 116 towards at least one stone. In an embodiment, the voltage generator 302 may generate high-voltage pulses effective to ignite electrical spark discharge in the electro-conductive fluid 104. For example, the high-voltage pulses may be in any waveform shape including square, triangular, or other shape.

The lithotripter apparatus 300 may also include a controller 304 operably coupled to the voltage generator 302. The controller 304 is configured to adjust operating parameters of the voltage generator 302, such as voltage, electrical pulse shape or duration, gap between two sequential electrical pulses, among others. The controller 304 may be further configured to switch the voltage generator 302 on/off.

The lithotripter apparatus 300 may also include a user interface device 306 configured to receive an input from a user and to send a signal to the controller 304. The user interface device 306 may be a display with a keyboard, touch screen, or other input device. A user may provide or input operating parameters, such as electric voltage and pulse duration, among others. For example, the controller 304 and the user interface device 306 may form a computing device, such as a desktop or laptop computer, through which an operator may input instructions to the electro-hydraulically actuated lithotripter 100 to control the operation thereof according to any method disclosed herein.

The electro-hydraulically actuated lithotripters disclosed herein may fragment a stone with minimal collateral damage to surrounding tissue by using high-voltage pulses. The electro-hydraulically actuated lithotripter may be inserted into a biliary or a urinary system of a human body (e.g., a ureter) via a catheter or endoscope in order to at least partially destroy stones, such as kidney stones, gallstones, cystine stones, and other calculi.

Figure 4:
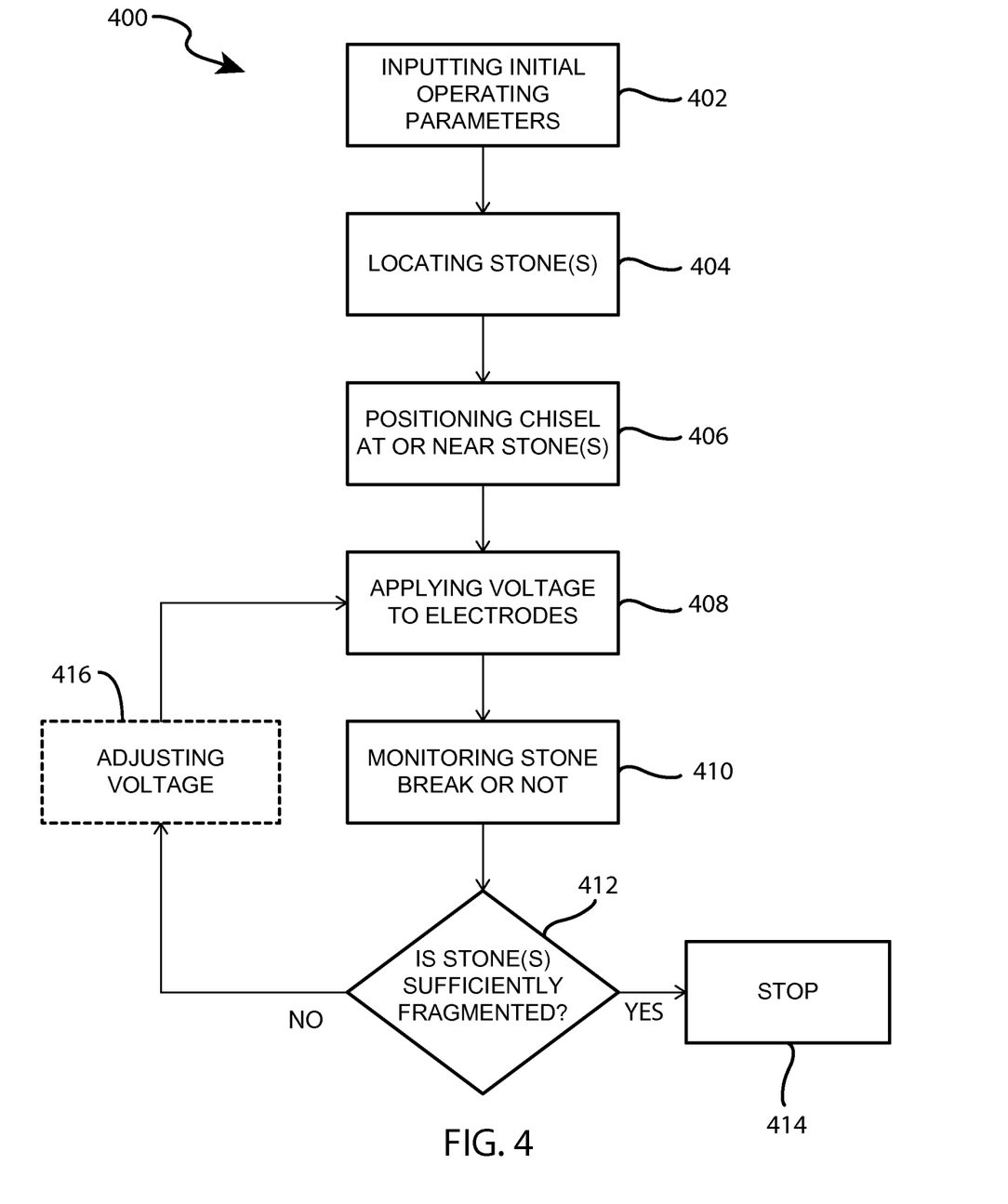
FIG. 4 is a flow chart illustrating a method of fragmenting a kidney stone according to an embodiment.

FIG. 4 is a flow chart illustrating a method 400 of fragmenting stone(s) according to an embodiment. The method 400 may include inputting initial operating parameters for the electro-hydraulically actuated lithotripter at operation 402. For example, the operating parameter may include voltage, pulses, gap between pulses, combinations thereof, etc. to be applied to the proximal electrode 114 and the distal electrode 112 shown in FIG. 2. For example, treatment for a patient may start at a relatively low voltage level, with a long gap between electric pulses, in order to accustom the patient to the sensation. The length of the gap between the pulses may also be controlled to allow cavitation bubbles to disperse, which may minimize tissue damage.

The method 400 may also include locating stone(s) at operation 404. A fluoroscopic x-ray imaging system or an ultrasound imaging system may be used to locate the stones and monitor the fragmentation of the stone(s) during the procedure.

The method 400 may further include positioning the chisel 116 to be at (e.g., in contact with) or near the stone(s) at operation 406. For example, the imaging system may be used to enable selectively positioning the chisel 116 of the electro-hydraulically actuated lithotripter 100 near or in contact with the stone(s). The chisel 116 may be positioned using an endoscope, a catheter, or another suitable device.

The method 400 further includes applying an effective voltage to electrodes (e.g., the proximal and distal electrodes 114 and 112 shown in FIG. 2) at operation 408 that causes electrical discharge into the electro-conductive fluid 104 and resultant acceleration of the chisel 116 (e.g., toward the stone(s)). Once the chisel 116 is positioned near or in contact with the stone(s), the impact energy from the chisel 116 may fragment the stone(s). Because the high pressure wave or shock wave is contained within the chamber 102 and the motion of the chisel 116 is restricted to very small distances and limited directions, the risk of urological or other injury may be reduced in a patient.

The method 400 may further include monitoring the stone(s) to observe if the stone(s) is fragmented at operation 410. For example, the imaging system (e.g. the X-ray imaging system or the ultrasound imaging system) may be able to produce an image of the stone(s). The image of the stone(s) may change from a distinct bright or dark spot to a fuzzy cloud as the stone is disintegrated into a fine powder. The image of the stone(s) may be used to determine if the stone(s) are sufficiently fragmented at operation 412. If the stone(s) is sufficiently broken-up, then method 400 may stop at operation 414. If the stone(s) is not sufficiently fragmented, the voltage may optionally be adjusted at operation 416 and the method 400 may further include applying the voltage at operation 408. This cycle may be repeated until the stone(s) breaks into sufficiently small pieces. By applying a number of high-voltage pulses, the stone(s) may be eventually fragmented.

The adjustment in voltage may be needed for one or more of the following reasons. The operation may require higher voltage pulses or more pulses to fragment a relatively larger stone(s) compared to a relatively smaller stone(s). Additionally, the voltage from the voltage generator 302 may affect the number of pulses. For example, a higher voltage may reduce the number of pulses for the same size stone(s). For example, the voltage may be in the order of magnitude of about 1 kV to about 6 kV, such as about 1 kV to about 4 kV, or about 2.5 kV to about 3.5 kV. Additionally, the power level may also depend on the patient's pain threshold and the observed success of stone breakage. The patient may be sedated during the procedure, such that the power levels may be brought up more quickly at a much higher pulse frequency.

It will be appreciated the lithotripter apparatuses disclosed herein may also be used for other living bodies besides humans, such as non-human animals as well. Accordingly, the operating parameters for the lithotripter apparatuses may vary accordingly based on the patient and animal type.

While various aspects and embodiments have been disclosed herein, other aspects and embodiments are contemplated. The various aspects and embodiments disclosed herein are for purposes of illustration and are not intended to be limiting.

What is claimed:

1. A lithotripter apparatus for fragmenting at least one stone in a body during medical treatment, the lithotripter apparatus comprising:
    a chamber configured to contain an electro-conductive fluid therein, the chamber including a proximal end wall and a distal end wall longitudinally spaced from the proximal end wall, the chamber configured to expand substantially in a longitudinal direction; and
    an intermediate portion therebetween;
    a chisel coupled to the chamber and located at least proximate to the distal end wall;
    a proximal electrode located at least partially in the chamber; and
    a distal electrode located at least partially in the chamber and spaced from the proximal electrode;
    wherein responsive to an effective voltage applied between the proximal and distal electrodes, the proximal and distal electrodes are configured to electrically discharge into the electro-conductive fluid to generate shock waves in the chamber that expand the chamber substantially in the longitudinal direction and accelerate the chisel; and
    wherein at least one of:
        the chisel is attached to the distal electrode, and the distal electrode is coupled to the distal end wall;
        the chisel is integral with the distal electrode;
        the distal electrode is coupled to the distal end wall; or
        the chamber is configured to expand substantially entirely in the longitudinal direction.

2. The lithotripter apparatus of claim 1 wherein the distal end wall of the chamber is thinner than the proximal end wall of the chamber such that the proximal end wall does not substantially expand responsive to the shock waves, while the distal end wall expands in a longitudinal direction responsive to the shock waves.

3. The lithotripter apparatus of claim 2 wherein responsive to the shock waves, the chisel moves outwardly in the longitudinal direction by a distance of about 0.50 mm to about 1.5 mm.

4. The lithotripter apparatus of claim 2 wherein responsive to the shock waves, the chisel moves outwardly in the longitudinal direction by a distance of about 0.75 mm to about 1 mm.

5. The lithotripter apparatus of claim 2 wherein the intermediate portion of the chamber is configured as a bellows to provide flexibility to the chamber in the longitudinal direction.

6. The lithotripter apparatus of claim 1 wherein the electro-conductive fluid is substantially sealed within the chamber.

7. The lithotripter apparatus of claim 1 wherein the electro-conductive fluid includes water and one or more salts.

8. The lithotripter apparatus of claim 1 wherein the proximal end wall of the chamber includes an opening therein, and the proximal electrode extends inwardly through the opening and into the chamber.

9. The lithotripter apparatus of claim 1 wherein the chisel is attached to the distal end wall.

10. The lithotripter apparatus of claim 1 wherein each of the proximal electrode and the distal electrode includes at least one material selected from a group consisting of copper, copper alloys, aluminum, aluminum alloys, silver, silver alloys, gold, and gold alloys.

11. The lithotripter apparatus of claim 1 wherein the chisel includes at least one of steel, stainless steel, titanium, or tungsten carbide.

12. The lithotripter apparatus of claim 1 wherein the chamber is substantially impermeable to the shock waves.

13. The lithotripter apparatus of claim 1 wherein the chamber includes at least one of an electrical insulator or a metallic material.

14. The lithotripter apparatus of claim 1, further comprising:
    a voltage generator configured to generate the effective voltage; and
    a controller operably coupled to the voltage generator.

15. The lithotripter apparatus of claim 14, further comprising an interface device operably coupled to the controller and configured to receive input from a user and send a signal to the controller with the input.

16. The lithotripter apparatus of claim 15, wherein the input includes voltage and pulse duration to be generated by the voltage generator.

17. The lithotripter apparatus of claim 1, further comprising a first electrical connection coupled to the proximal electrode and a second electrical connection coupled to the distal electrode.

18. A method of using a lithotripter apparatus for fragmenting at least one stone in a body during medical treatment, the method comprising:
    positioning a chisel at or near the at least one stone in the body, the chisel coupled to a chamber containing an electro-conductive fluid therein, the chamber including a proximal end wall and a distal end wall longitudinally spaced from the proximal end wall; and applying a voltage between a proximal electrode located at least partially in the chamber and a distal electrode located at least partially in the chamber and spaced from the proximal electrode, thereby causing electrical discharge into the electro-conductive fluid from the proximal electrode and the distal electrode and generation of shock waves in the chamber that expand the chamber in a longitudinal direction and accelerate the chisel toward the at least one stone;

wherein at least one of:
the chisel is attached to the distal electrode, and the distal electrode is coupled to the distal end wall;
the chisel is integral with the distal electrode;
the distal electrode is coupled to the distal end wall; or
the chamber is configured to expand substantially entirely in the longitudinal direction.

19. The method of claim 18, further comprising locating the at least one stone within the body using an imaging system.

20. The method of claim 19 wherein the imaging system includes at least one of a fluoroscopic x-ray imaging system or an ultrasound imaging system.

21. The method of claim 19, further comprising, via the imaging system, monitoring the at least one stone to determine if the stone is fragmented.

22. The method of claim 21, further comprising adjusting the voltage applied to the proximal electrode and the distal electrode in response to monitoring the at least one stone.

23. The method of claim 18 wherein the chamber includes a proximal end wall, a distal end wall spaced from the proximal end wall, and an intermediate portion therebetween, the chisel coupled to the chamber at least proximate to the distal end wall.

24. A lithotripter apparatus for fragmenting at least one stone in a body during medical treatment, the lithotripter apparatus comprising:

a chamber configured to contain an electro-conductive fluid therein, the chamber including a proximal end wall, a distal end wall spaced from the proximal end wall, and an intermediate portion therebetween;

a chisel coupled to the chamber and located at least proximate to the distal end wall;

a proximal electrode located at least partially in the chamber; and a distal electrode coupled to the distal wall, located at least partially in the chamber, and spaced from the proximal electrode;

wherein responsive to an effective voltage applied between the proximal and distal electrodes, the proximal and distal electrodes are configured to electrically discharge into the electro-conductive fluid to generate shock waves in the chamber that accelerate the chisel.

* * * * *